United States Patent [19]

Orr

[11] Patent Number: 4,674,495

[45] Date of Patent: Jun. 23, 1987

[54] CATHETER WITH INSUFFLATION LUMEN

[75] Inventor: Douglas P. Orr, Glens Falls, N.Y.

[73] Assignee: Mallinckrodt, Inc., St. Louis, Mo.

[21] Appl. No.: 666,322

[22] Filed: Oct. 31, 1984

[51] Int. Cl.⁴ ............................................ A61M 16/00
[52] U.S. Cl. ........................... 128/207.14; 128/207.15;
128/912; 604/26; 604/93
[58] Field of Search ...................... 128/207.15, 207.16,
128/200.26, 912, 207.14; 604/96–103, 26, 93

[56] References Cited

U.S. PATENT DOCUMENTS

| | | | |
|---|---|---|---|
| 334,316 | 1/1886 | Ward et al. | 604/96 |
| 1,922,084 | 8/1933 | Gerow | 604/102 |
| 2,930,377 | 3/1960 | Cowley | 604/103 |
| 3,385,301 | 5/1968 | Harautuneian | 604/103 |
| 3,438,375 | 4/1969 | Ericson | 604/98 |
| 3,625,793 | 12/1971 | Sheridan | 604/101 |
| 4,159,722 | 7/1979 | Walker | 128/207.15 |
| 4,214,593 | 7/1980 | Imbruce et al. | 604/96 |
| 4,300,550 | 11/1981 | Gandi et al. | 604/26 |
| 4,305,392 | 12/1981 | Chester | 128/207.15 |
| 4,329,994 | 5/1982 | Cooper | 604/98 |
| 4,584,998 | 4/1986 | McGrail | 128/207.15 |

Primary Examiner—Henry J. Recla
Attorney, Agent, or Firm—Bernard, Rothwell & Brown

[57] ABSTRACT

A catheter includes a tubular member forming a primary lumen and having an insufflation lumen formed in the wall thereof. The insufflation lumen is of somewhat D-shape with the generally flat side being radially inward and the curved side being radially outward. A communicating tube, which is provided for connection to the proximal opening of the insufflation lumen, is made, at least at the end thereof connected to the insufflation lumen, of a cross-sectional shape approximating that of the insufflation lumen. The generally flat side of this tube is aligned with the generally flat side of the insufflation lumen and the curved radially outward side is aligned with the corresponding side of the insufflation lumen. The communicating tube, at least in the region of connection to the insufflation lumen, is made of a relatively rigid material so as to resist deformation and resultant restriction of the internal cross-section thereof. Because of the making of the communicating tube with a generally flat side disposed inwardly, there is a much lesser tendency for the rigid end of the communicating tube, when inserted into the proximal opening, to cause a bulge in the internal cross-section of the primary lumen.

4 Claims, 8 Drawing Figures

U.S. Patent  Jun. 23, 1987  4,674,495
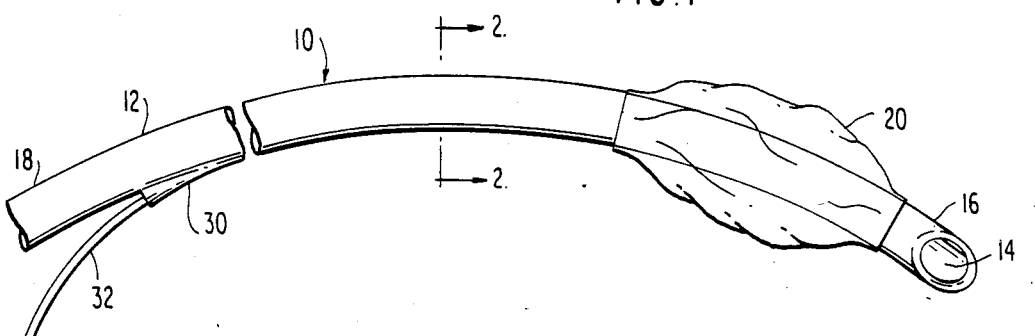
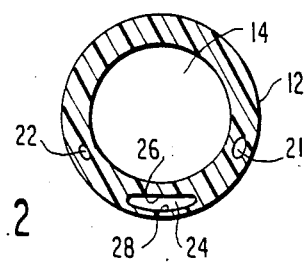
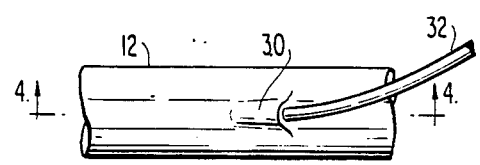
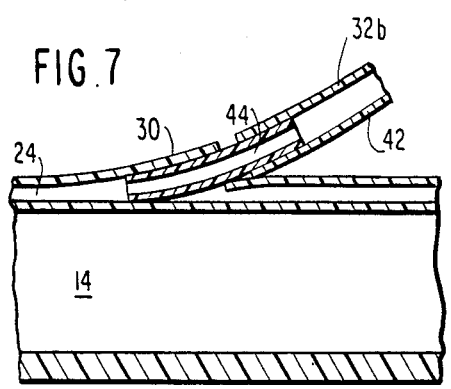
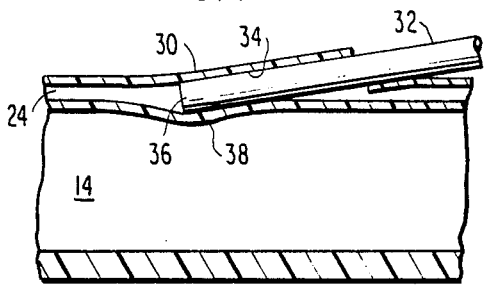
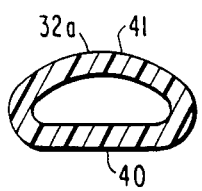
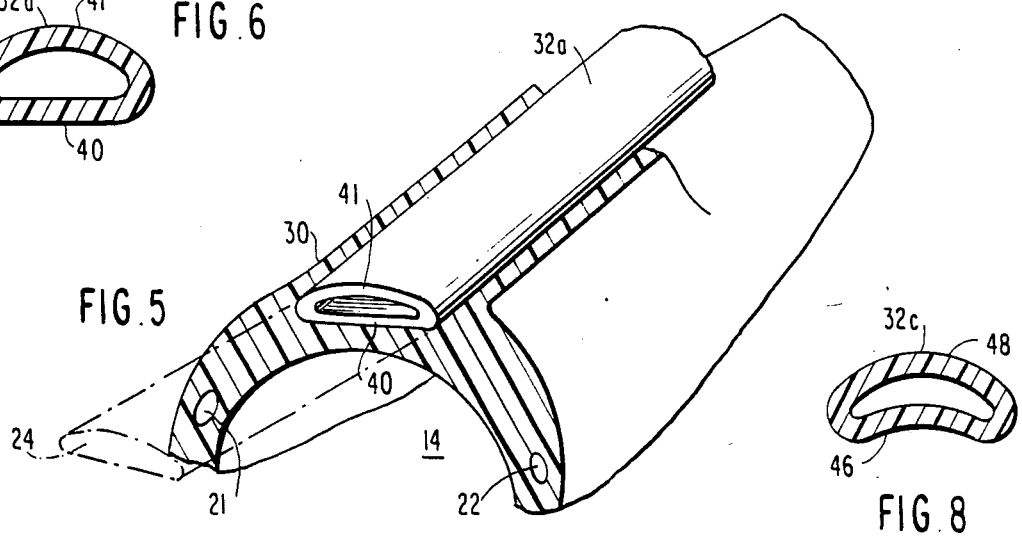
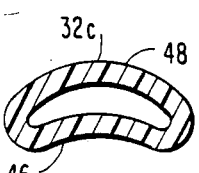

CATHETER WITH INSUFFLATION LUMEN

BACKGROUND OF THE INVENTION

1. Field of the Invention

This invention relates to catheters and, more particularly, to catheters including an insufflation lumen for supplying humidified gas to a patient.

2. Description of the Prior Art

Catheters are employed for many purposes to provide for passage of fluids to and from the human body. One form of such catheter, more commonly referred to as a tracheal tube, is adapted to be inserted through the oral cavity of a patient and through the trachea to provide for the supply of fluids to the body and for the monitoring of internal conditions in the body and to provide for removal of secretions from within the body. In many cases it is desirable to supply a gas such as oxygen to a patient and it is also desirable that the humidity of the gas so supplied be controlled with reasonable accuracy. Where a gas such as oxygen is supplied to a patient, this is accomplished in many cases by supplying such gas in volumes corresponding to normal respiration through the central aperture, that is, the primary lumen of the catheter, and this over a long period of time was the conventional manner of supplying such gas.

In more recent years there has been a great deal of interest in a new method of ventilating patients, called high frequency jet ventilation (HFJV). In this procedure the gas, instead of being supplied in volumes corresponding to normal respiration, is supplied in small spurts at pressures that are normally higher than those used in conventional ventilation, and the gas is ordinarily supplied through an insufflation lumen provided in the wall of the catheter or through a separate small catheter or needle rather than through the central or primary lumen. Because of the higher pressures employed in HFJV and because of the smaller cross-sectional area of the insufflation lumen compared to that of the primary lumen any significant restriction in the path providing communication to and through the insufflation lumen may cause a significant drop in pressure of the gas as it passes beyond such restriction. This poses a particular problem, as described below, when humidified gas is supplied to a patient, because such a drop in pressure proportionately varies the relative humidity.

The insufflation lumen is ordinarily provided with an opening through the wall of the catheter in the distal region of the catheter for communicating with the lungs of the patient. Further, this lumen is usually formed with an opening in the proximal region of the catheter for receiving a communicating tube, which in turn can be connected to a source of humidified gas. This communicating tube is connected in sealed relationship with the proximal opening of the insufflation lumen in any of a number of ways. For example, it may be connected thereto in the manner set forth in Sheridan et al. Pat. No. 3,625,793, which is assigned to the assignee of the subject application.

In accordance with the process set forth in the Sheridan et al. patent a heated mandrel is inserted into the proximal opening to expand this opening and the communicating tube is inserted into this opening promptly thereafter so that, upon contraction of the catheter material around the proximal opening, a sealing fit is formed with the end of the communicating tube. If the communicating tube is formed of a relatively flexible material the contracting forces around the proximal opening squeeze the communicating tube so as to reduce its internal diameter in the region of the proximal opening. As a result of this restriction there tends to be a significant drop in pressure as the insufflation gas passes beyond this restriction and as a result the relative humidity of the insufflation gas being supplied drops to a significantly lower value. For example, should the gas be supplied at say 2 atmospheres and should the pressure drop to 1 atmosphere beyond the restricted area, the relative humidity of the gas being supplied decreases to approximately one-half its original value. Since the amount of the contraction of the internal diameter of the connecting tube is unpredictable and uncontrollable in such a manufacturing operation the user would be faced with lack of knowledge of the humidity of the gas actually reaching the patient. This is very undesirable.

In lieu of the process described above for connecting the communicating tube to the proximal opening, such connection may be accomplished by means of suitable glue or solvent which acts on the plastic of which the catheter and the communicating tube are formed. In such case it is conventional to first enlarge the proximal opening of the insufflation lumen so as to facilitate insertion of the communicating tube. In this case, when the solvent is applied to the abutting surfaces, the wall of the catheter at the proximal opening tends, because of the elastic memory of the plastic of which it is formed, to return toward its original size. This, as in the above-described arrangement utilizing the process of the Sheridan patent, also results in a restriction of the internal diameter of the communicating tube. This gives rise to the same problem as that just discussed.

One proposed solution to this problem has been to form the communicating tube of a more rigid material so as to resist contraction under the force exerted by the wall of the catheter surrounding the proximal opening and thus to eliminate restriction in the internal diameter of the communicating tube or to substantially limit the amount of such restriction. This, however, gave rise to an additional problem in connection with the primary lumen of the catheter. When such a rigid connecting tube is inserted into the proximal opening it has a tendency to force the wall of the primary lumen inwardly, thereby modifying the internal shape of the lumen at that point and reducing the cross-sectional area of the primary lumen with consequent restriction of flow of fluid therethrough. Further it is important to have a uniform cross-section throughout the length of the primary lumen to facilitate the passage of components, such as suction catheters, therethrough.

By the present invention both of these problems are eliminated and a catheter is provided in which there is no significant restriction of the internal diameter of the communicating tube and in which there is no inward bulge and restriction in the primary lumen.

Accordingly, it is an object of this invention to provide a catheter including an insufflation lumen which facilitates the providing of gas through the insufflation lumen at controlled pressure and relative humidity.

It is another object of this invention to provide a catheter which avoids restriction in the tube for supplying humidified gas from a suitable source to the insufflation lumen.

It is a further object of this invention to provide a catheter construction in which the communicating tube for supplying gas to the insufflation lumen not only has no restriction therein but further does not adversely affect the cross-sectional area of the primary lumen of the catheter.

SUMMARY OF THE INVENTION

In carrying out this invention, in one form thereof, a catheter is provided which includes a tubular member having a central passage, or primary lumen, therein. The catheter includes in the wall thereof an insufflation lumen having a sufficient cross-sectional area to provide for supplying of gas through the insufflation lumen to the patient in the desired quantity and at the desired pressure and humidity. In order to provide for the supply of sufficient gas through the insufflation lumen and yet confine the insufflation lumen within the space between the inner and outer walls of the tubular member forming the catheter, the insufflation lumen, unlike other secondary lumens such as irrigation lumen, monitoring lumen, inflation lumen, etc., is not made of circular cross-section but, rather, is made of somewhat flattened cross-section, extending substantially further in the circumferential direction of the tubular member than in the radial direction. In carrying out this invention, the communicating tube, which is provided for connection to the proximal opening of the insufflation lumen, is made, at least at the point of connection to the proximal opening of the insufflation lumen, of a cross-sectional shape approximating that of the insufflation lumen itself. More specifically, the insufflation lumen is of somewhat D-shape with the generally flat side being radially inward and the curved side being radially outward, and the end of the communicating tube connected to the insufflation lumen is made with a corresponding cross-sectional shape with the generally flat side being aligned with the generally flat side of the insufflation lumen and the curved radially outward side being aligned with the corresponding side of the insufflation lumen. The communicating tube is made of a relatively rigid material so as to resist deformation and resultant restriction of the internal cross-section thereof. However, because of the making of the cross-sectional shape of the communicating tube as described above with the flat side disposed inwardly, there is a much lesser tendency for the end of the communicating tube, when inserted into the proximal opening, to cause a bulge or deformation in the internal cross-section of the primary lumen of the catheter.

BRIEF DESCRIPTION OF THE DRAWINGS

FIG. 1 is a general representation of a portion of a catheter incorporating an embodiment of this invention;

FIG. 2 is an enlarged sectional view taken along the line 2—2 in FIG. 1;

FIG. 3 is a side view of a portion of a catheter tube constructed in the conventional manner of the prior art;

FIG. 4 is an enlarged sectional view taken along the line 4—4 in FIG. 3;

FIG. 5 is an enlarged view, partly in section, of a portion of a catheter illustrating the communicating tube of this invention connected to the proximal opening of the insufflation lumen of the catheter;

FIG. 6 is an enlarged sectional view of the communicating tube of this invention;

FIG. 7 is an enlarged longitudinal sectional view of a portion of the catheter and the communicating tube illustrating an adapter included in the assembly.

FIG. 8 is a view corresponding to FIG. 6 showing a modified cross-section of the communicating tube.

DESCRIPTION OF THE PREFERRED EMBODIMENT

Referring to FIGS. 1 and 2, there is shown a portion of a catheter 10 which includes a tubular member 12 having a central passage, or primary lumen, 14 through which respiratory gases may be supplied to a patient and through which secretions collecting within the body may be removed by suitable apparatus. The specific device illustrated is more frequently referred to as a tracheal tube because of its specific use, but it is referred to in this specification as a catheter because this is the generic term and also to avoid undue confusion through the use of the term "tube" in a multiple sense in the specification. The catheter has a distal end 16, including the distal end of the opening 14, and a proximal end 18. The catheter shown in these figures includes an inflatable cuff 20 which may be inflated in a conventional manner to engage the trachea of the patient.

In a conventional manner, as best shown in FIG. 2, the catheter includes a plurality of secondary lumens 21, 22 and 24 arranged between the inner and outer walls of the tubular member 12. In the form shown, the secondary lumen 21 may be a passage through which air is supplied to the interior of the cuff 20 to inflate the cuff for engagement with the trachea. The secondary lumen 22 may be employed for irrigation or monitoring in a conventional manner. The third secondary lumen shown in FIG. 2 is employed as an insufflation lumen through which a gas, for example, oxygen, may be supplied to the patient. The insufflation lumen usually includes an opening in the interior wall of the tube 12 in the distal region of the catheter, but this is not part of the present invention and illustration and description of the details thereof are omitted.

Since the insufflation lumen may have to carry a substantial volume of gas to the patient it conventionally is of a substantially greater size than the other secondary lumens. Because of this required size, if the insufflation lumen were made of circular cross-section it would necessitate, for adequate capacity, that the wall of the tubular member 12 be of substantially greater thickness than is normally permissible for comfort of the patient. As shown in FIG. 2, the insufflation lumen is formed in flattened D-shape and incldes a generally flat side 26 in a radially inward position and a curved side 28 in a radially outward position. This D-shape, while not essential, is advantageous because it provides the maximum cross-sectional area for the insufflation lumen while also minimizing bulging of the catheter wall toward either the inside or the outside. The larger dimension of the insufflation lumen extends generally circumferentially in the wall of the tubular member 12 and the smaller dimension extends radially. While in the preferred form shown in FIG. 2 the side 26 of the insufflation lumen is flat, the insufflation lumen may also be made with this side curved. As used in the description and claims of this specification, therefore, the term "generally flat" is intended to embrace an insufflation lumen in which the radially inward wall is flat, as shown in FIG. 2, or in which the radially inward wall is slightly curved.

At its proximal end the insufflation lumen is normally formed to project through the exterior wall of the tubular member 12 so as to provide a proximal opening in a boss 30. In order to supply gas to the insufflation lumen and thence to the patient, a communicating tube 32 is connected to the proximal opening of the insufflation lumen. The other end of the communicating tube 32 is adapted to be connected to a suitable source of supply of ventilating gas (not shown).

Referring now to FIGS. 3 and 4, the proximal opening of the insufflation lumen in the boss 30 is normally made by slightly enlarging the end of the proximal opening in order to receive a conventional communicating tube 32, which normally is of circular cross-section. This opening may be formed in the manner of the Sheridan patent described above or the connection of the communicating tube to the proximal opening of the insufflation lumen may be made by simply enlarging the proximal opening and then applying a suitable glue or solvent. In either case, if the communicating tube 32 is made of a conventional flexible material the contraction of the material of the tubular member 12 at the proximal opening upon cooling, or as a result of elastic memory where solvents are employed, results in a squeezing of the end of the communicating tube 32 and thereby results in a reduction in the internal diameter of the tube at that point. This results in an undesirable restriction in the passage in the tube 32. As described above, when this occurs it causes a variation in pressure and in the relative humidity of the gas supplied to the patient. Thus the gas may be supplied at a relative humidity which may differ substantially from that desired for the patient. For example, if insufflation gas should be supplied to the patient at say 80% relative humidity, and the gas at the source is supplied at this relative humidity and if the aforementioned restriction should result in a drop in pressure to approximately half that of the source of insufflation gas, then the relative humidity of the gas actually supplied to the patient will in turn be approximately half that of the source of insufflation gas, i.e., 40%. More importantly, since the amount of this contraction may vary from catheter to catheter the user cannot reliably depend upon the gas supplied to the patient having specific desired characteristics. Further, where the communicating tube is made of the conventional circular cross-section, the passage therein is smaller than the width of the flattened D-shaped insufflation lumen and full advantage is not taken of the size of the insufflation lumen.

The aforementioned contraction could be avoided by employing a more rigid material for the communicating tube in the form shown in FIG. 4. As there shown if a sufficiently rigid material is supplied, the contractive forces exerted by the material of the tubular member 12 at the proximal opening 34 in the boss 30 will have relatively little effect on the communicating tube 32 and the internal diameter thereof will not be affected. As a result, there is substantially no restriction in the communicating tube 32 and the pressure and relative humidity of the insufflation gas are reliably maintained.

However, as also illustrated in FIG. 4, the use of a rigid material for the communicating tube 32 has a side effect which also gives an undesirable characteristic to the catheter. Specifically, as shown in FIG. 4, the tip 36 of the communicating tube 32, because of the stiffness or rigidity thereof, tends to force the wall of the primary lumen inwardly, as indicated at 38, thereby providing an undesirable restriction in the primary lumen which adversely affects the flow of fluids therethrough. Further, the resulting non-uniform internal cross-section renders difficult the passage of components, such as suction catheters, therethrough.

By the present invention both of these undesirable adverse results are avoided and a catheter, with an insufflation lumen, is provided which insures a reliable supply of insufflation gas at a dependable pressure and relative humidity and which insures against any restriction in the primary lumen 14 which could adversely affect the proper functioning of the primary lumen. Specifically, the communicating tube 32a, as shown in FIGS. 5 and 6, is made of a shape in cross-section substantially corresponding to that of the insufflation lumen 24. More specifically, the cross-section of the communicating tube 32a is made of flattened D-shape with one wall 40 being generally flat and with the second wall 41 being curved. The generally flat wall 40 is disposed on the inward side of the communicating tube 32a so as to be generally aligned with the corresponding radially inward, generally flat side 26 of the insufflation lumen 24. The outward curved wall 41 is aligned with, and corresponds generally in shape to, the curved radially outward wall 28 of the insufflation lumen.

The communicating tube 32a is made of a rigid or stiff material so that any contraction of the wall of the tubular member 12 at the proximal opening does not effect any significant contraction of the communicating tube 32a, nor result in any restriction in the internal diameter thereof. However, because of the formation of the communicating tube 32a with the cross-sectional shape shown and more specifically with the generally flat side 38 shown in FIG. 5 there is no significantly projecting tip, such as the tip 36 shown in FIG. 4, which results when a communicating tube of circular cross-section is employed. As a result there is no significant tendency for the inner wall 40 of the communicating tube 32a to effect a bulge, such as that shown at 38 in FIG. 4, in the primary lumen, even though the communicating tube 32a is made of a relatively rigid material rather than a flexible material. Thus, by this invention both of the aforementioned adverse affects referred to above are eliminated. Restriction of the internal passage in the communicating tube is avoided because of the relatively rigid or stiff material employed, so that insufflation gas may be supplied therethrough with confidence that it is being received by the patient at the desired pressure and relative humidity. Further, when the communicating tube is assembled in sealing relationship with the proximal opening 34 of the insufflation lumen no inward bulging of the inner wall of the primary lumen occurs and hence there is no restriction in the primary lumen which could have any adverse affect on the proper functioning of this lumen.

While, for convenience of illustration and description, the communicating tube 32a has been shown as having an integral structure with its end extending into the proximal opening in the boss 30, in actual practice of the invention applicant prefers to make the communicating tube as a two-part sub-assembly, as shown in FIG. 7. As there shown, the communicating tube, generally designated as 32b, includes a major part 42 extending to a source (not shown) of insufflation gas and an adapter 44 which is received in the opening in the boss 30. The adapter 44 in this case is made of the relatively stiff or rigid material, as described above, and the major portion 42 is made of a flexible material which is more convenient for connecting to a source of insufflation gas.

In a specific embodiment of the applicant's invention the tubular member 12 comprising the main body of the catheter is formed of a plasticized polyvinylchloride having durometer hardness of 84 Shore A and a specific gravity of 1.2391. The adapter is made of a plasticized polyvinylchloride having a durometer hardness of 60.8 Shore D and a specific gravity of 1.2936.

In the embodiment just described the radially inward sides 26 and 40 of the insufflation lumen 24 and communicating tube 32a, respectively, are shown as generally flat. The insufflation lumen of a catheter may in some cases be made so that the radially inward wall is slightly curved in a direction corresponding somewhat to the wall of the primary lumen with this inner wall of the insufflation lumen being, therefore, slightly convex. In that case, as shown in FIG. 8, the radially inward wall 46 of the communicating tube 32c would be made correspondingly curved so that the inner wall of the passage therethrough would also be slightly convex and the cross-section would correspond to that of the insufflation lumen with which it is used. The radially outward wall 48 has a greater curvature than the wall 46. As indicated above, the term "generally flat" employed in the description and claims is intended to embrace both a communicating tube, as shown in FIG. 6, having a flat inward wall and a communicating tube as shown in FIG. 8, in which the inward wall is slightly curved.

It is claimed:

1. A catheter comprising a tubular member having a central lumen and an insufflation lumen within the wall of said tubular member, the proximal end of said insufflation lumen terminating in a proximal opening extending through the exterior surface of said wall, and a communicating tube received in said proximal opening for communicating the insufflation lumen with a source of insufflation gas,
   (a) said insufflation lumen being of flattened generally D-shaped cross-section and including a generally flat radially inward side and a curved radially outward side, the larger dimension of said generally D-shaped insufflation lumen extending generally circumferentially in said wall;
   (b) said communicating tube having a generally D-shaped cross-section substantially conforming to the cross-section of said insufflation lumen and including a generally flat radially inward side aligned with the corresponding side of said insufflation lumen;
   (c) at least the portion of said communicating tube which is received in said proximal opening being formed of a rigid material to resist contraction of said communicating tube by forces exerted by the wall of said tubular member at said proximal opening.

2. The catheter of claim 1 in which said radially inward side of said insufflation lumen and said radially inward side of said communicating tube are flat.

3. The catheter of claim 1 in which said radially inward side of said insufflation lumen and said radially inward side of said communicating tube are curved in a direction providing convex radially inward sides and said radially outward sides have a greater curvature than said radially inward sides.

4. The catheter of claim 1 in which said communicating tube comprises a major portion formed of flexible material and an adapter received in said proximal opening and formed of a rigid material.

* * * * *